United States Patent

Szakács et al.

Patent Number: 5,240,901
Date of Patent: Aug. 31, 1993

[54] METHOD AND COMPOSITION FOR PROTECTING PLANTS AGAINST STRESS AND/OR FOR INCREASING THEIR YIELD

[75] Inventors: László Szakács, Soltvadkert; Etelka Szabó née Mig, Kiskörös; Demeter Lásztity, Budapest; Ferenc Pribék, Budapest; László Szigmond, Budapest, all of Hungary

[73] Assignee: Reanal Finomvegyeszergyar, Budapest, Hungary

[21] Appl. No.: 785,208

[22] Filed: Oct. 24, 1991

Related U.S. Application Data

[62] Division of Ser. No. 407,921, Sep. 15, 1989, abandoned.

[30] Foreign Application Priority Data

Nov. 18, 1988 [HU] Hungary .................. 2251-5950/88

[51] Int. Cl.$^5$ ............................................ A01N 31/02
[52] U.S. Cl. .................................................. 504/320
[58] Field of Search ...................... 71/98; 504/320, 349

[56] References Cited

FOREIGN PATENT DOCUMENTS 49-94847 1/1973 Japan .
0146766 11/1979 Japan .

OTHER PUBLICATIONS

McRorie et al. "Isolation and Identification of a Naturally Occurring Analog of Methianine" *Plant Growth Substances* 1979, F. Skoog, Ed. pp. 115-118.
Even-Chen et al. "Inhibition of Ethylene Biosynthesis by Aminoethoxyvinylglycine and by Polyamines Shunts Label from 3,4-[$^{14}$C]Methianine into Spermidine in Aged Orange Peel Discs" Plant Physiol. (1982), 69, 385-388.
Merck Index, 10th Ed. Compound 2855 p. 415 (1983).
Novenyvedoszerek Szerek Mutragyak (Plant Protecting Agents and Artificial Fertilizers), pp. 1, 58, 64, 268, Mezogazdasagi Kiado Budapest (1986).

*Primary Examiner*—Glennon H. Hollrah
*Assistant Examiner*—Brian M. Burn
*Attorney, Agent, or Firm*—Herbert Dubno; Jonathan Myers

[57] ABSTRACT

The invention relates to a method for protecting plants against stress or for increasing their yield, in which the plant is treated in its intense development stage or directly after flowering or before, during or maximum 5 days after the occurrence of stress with 0.001-10 kg/hectare of a compound of Formula (I),

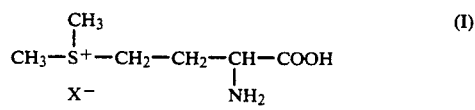

wherein X$^-$ is an agriculturally acceptable inorganic or organic anion. The invention also relates to a composition for protecting plants against stress or for increasing their yield, which comprises as active ingredient 0.001-95% by weight of a compound of formula (I).

4 Claims, No Drawings

METHOD AND COMPOSITION FOR PROTECTING PLANTS AGAINST STRESS AND/OR FOR INCREASING THEIR YIELD

This is a divisional of co-pending application Ser. No. 07/407,921 filed on Sep. 15, 1989, now abandoned.

FIELD OF THE INVENTION

The invention relates to a method and composition for protecting plants against stress and/or for increasing their yield.

BACKGROUND OF THE INVENTION

As known, ethylene production of plant tissues increases upon the effect of cold, physical or chemical damages and microbial or insect infections (plants 120, 63-69 1974). In general, it can be laid down as a fact that plants react with increased ethylene production to all environmental factors affecting their normal development, such as meteorological effects (heat, rain, fog, frost, wind, intense radiation, etc.), chemical effects (effects of herbicides, agricultural chemicals, etc.), and damage caused by microorganisms and animals (such as insects, mites, rodents, etc.). These factors are termed in the following as stress factors. Ethylene overproduction leads to the disintegration of the semipermeable lipid-polysaccharide double walls of membranes and cells, which involves the premature ageing of plant cells and tissues, whereupon the vegetation period decreases and/or the metabolism slows down (Plant Physiol. 68, 594-596 1981). Ethylene production involves a decrease in cell protein and RNS content (Plant Physiol. 69, 385-388 1982). Upon ethylene overproduction provoked by stress factors the plant cells collapse energetically, which necessarily leads to a decrease in yield. Such a decrease in yield may appear e.g. as a loss in crop yield, stunting, slow growth, anamorphosis, etc.

SUMMARY OF THE INVENTION

Now it has been found, unexpectedly, that S-methyl-methionine sulphonium salts can be applied with excellent results to protect plants against stress and to avoid any decrease in yield attributable to stress factors. Upon treating the plant with an S-methyl-methionine sulphonium salt, its yield becomes practically independent of stress factors, and the yield level reaches the expectable maximum in respect to both quantity and quality.

Based on the above, the invention relates to a method for protecting plants against stress and/or for increasing their yield. According to the invention the plant is treated in its intense development stage and/or directly after flowering and/or before, during or maximum 5 days after the occurrence of stress with 0.001-10 kg/hectare of a compound of formula (I),

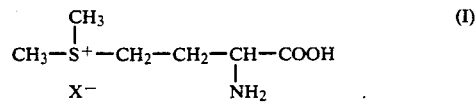

wherein $X^-$ is an agriculturally acceptable inorganic or organic anion.

The invention also relates to a composition for protecting plants against stress and/or for increasing their yield, which comprises as active ingredient 0.001-95% by weight of at least one compound of formula (I), wherein $X^-$ is as defined above, together with a solid or liquid carrier or diluent, optionally with one or more agriculturally acceptable additive and optionally with one or more known agricultural chemical applied in the treatment of the plant in question.

In the above formula $X^-$ may represent an anion derived from a mineral acid (such as from a hydrohalide, sulfuric acid, phosphoric acid or nitric acid) or from an organic acid (such as a lower carboxylic acid, a long-chained fatty acid or a sulphonic acid). With polyvalent anions, such as sulphate or phosphate ions, $X^-$ represents one equivalent of the anion in question.

The compounds of formula (I) have a chiral center thus they esist as optically active isomers and mixtures thereof, including racemic mixtures. Any of the individual isomers and any mixture thereof can be utilized in accordance with the invention.

S-Methyl-methionine sulphonium chloride (vitamin U) is a substance applied for pharmaceutical and veterinary purposes. S-Methyl-methionine sulphonium chloride can be isolated from its natural sources (such as raw cabbage-pickling brine or fruit juices) by extraction, e.g. as described in J. Am. Chem. Soc. 76, 115 (1954) and in U.S. Pat. No. 3,108,040. S-Methyl-methionine sulphonium salts formed with mineral acids can also be prepared synthetically e.g. as described in J. Biol. Chem. 207, 107 (1954), German patent No. 1,239,697 and Hungarian patent No. 179,752. S-Methyl-methionine sulphonium salts formed with organic acids can be prepared either as described in the papers cited just above, or can be obtained by subjecting another S-methyl-methionine sulphonium salt to anion exchange. Vitamin U is utilized in human therapy primarily in the prevention and healing of gastric and peptic ulcer (Bukin, V., Anisimov, V. E.: "Vitamin U", Izdatelstvo Nauka, Moscow, 1973), whereas in veterinary medicine it is applied primarily in the prevention and treatment of porcine esophagogastric ulcer (Hungarian patent No. 173,312; Magyar Állatorvosok Lapja (Journal of Hungarian Veterinarians; in Hungarian) 32, 555 1977).

No reference is given in the literature on the possible plant biological effects of vitamin U.

Without restricting the scope of the invention by theoretical considerations, we assume that the plant biological activity of vitamin U and of the other S-methyl-methionine sulphonium salts of formula (I) can be attributed to the fact that they provide a methionine source for ethylene production. Thereby these compounds do not impede the production of ethylene determined by the normal biological functions of the plant, but at the same time ethylene overproduction does not take place at the expense of the cell protein and RNS components. It should be noted, however, that the plant biological activity may also appear through another mechanism.

Depending on the plant culture, on the development stage of the plant and on the actual stress factor concerned, generally 0.01-1 kg/hectare of a compound of formula (I) is utilized in the treatment according to the invention. The treatment is performed preferably during the intense development stage of the plant, and is repeated directly after flowering. When the plant is to be protected against an acute stress (such as frost damage, pruning, chemical treatment, etc.), the plant is treated either before the occurrence of the stress expected, during the stress period, or shortly, preferably maximum 5 days, after the occurrence of stress.

The compound of formula (I) is applied onto the area to be treated as a solid or liquid composition. The most simple forms of liquid compositions are the aqueous solutions of the active agent; an aqueous solution ready for use may comprise the active agent generally in a concentration of 0.001–0.3% by weight. If desired, conventional additives, such as thickeners to prevent drifting, agents for improving resistance to rain (generally protecting colloids), and the like can also be added to the liquid compositions. The solid compositions may be e.g. powders or granulates, including sustained release granulates, which comprise, beside the active agent, one or more granular or powdery solid carrier or diluent (such as a clay mineral, talc, calcium carbonate, pumice stone, etc.), optionally together with other known additives, such as protecting polymers ensuring a sustained release for the active agent, agents increasing the adhesive power of the composition (such as mineral oils), and the like. To prepare a solid composition, it is preferred to use an active agent of formula (I) with poor water solubility.

The compositions according to the invention may also comprise, beside the active agent of formula (I), one or more additional agricultural chemical compatible with the S-methyl-methionine sulphonium salt present. These additional agricultural chemicals may be e.g. herbicides, insecticides, weed controlling agents, fungicides or fertilizers. Utilizing such multicomponent compositions the treatment according to the invention can be performed simultaneously with a conventional chemical treatment of an other purpose, and it has the additional advantage that, due to the presence of the compound of formula (I), the plants can be protected directly against the stress caused by the chemical treatment. The second or more additional active agent may be present in such a multicomponent composition generally in the same concentration as it would be present when applying it alone.

The invention is elucidated in detail by the aid of the following non-limiting Examples.

EXAMPLE 1

1 kg of S-methyl-methionine sulphonium chloride and 3 kg of Dikamine are dissolved in 200 liters of water. A spray solution is obtained, which can be diluted with water prior to use, if necessary.

EXAMPLE 2

1 kg of S-methyl-methionine sulphonium chloride and 0.5 kg of Decis are dissolved in 50 liters of water. A spray solution is obtained, which can be diluted with water prior to use, if necessary.

EXAMPLE 3

Maize plants growing on a parcel of 5 hectares were sprayed, at their development stage of 10–12 leaves, with 250 liters of a 0.2% by weight aqueous solution of S-methyl-methionine sulphonium chloride. The treatment was performed in a droughty period. The crop yield harvested from the treated parcel was higher by 17% than that harvested from an untreated parcel of the same area.

EXAMPLE 4

Sunflower plants growing on a parcel of 100 m² heavily overgrown with weeds were sprayed, at their development stage of 10–14 leaves, with a 0.2% by weight aqueous solution of S-methyl-methionine sulphonium chloride. The solution was sprayed onto the plants by rows from a hand-operated back spray equipment. The crop yield harvested from the treated parcel was 3,400 kg/hectare, whereas a crop yield of 1,900 kg/hectare was harvested from an untreated parcel of the same area.

EXAMPLE 5

Tomato and cucumber plants forced in a greenhouse were treated with a 0.2% by weight aqueous solution of S-methyl-methionine sulphonium chloride. The stem height of the treated plants was greater by 20–40 cm than that of the controls, and the resistance of the treated plants against powdery mildew and downy mildew increased considerably.

EXAMPLE 6

Paprika seedlings cultivated in a greenhouse were sprayed after setting out with a 0.2% by weight aqueous solution of S-methyl-methionine sulphonium chloride. In contrast to the controls, all of the treated seedlings took root, and no withering could be observed.

EXAMPLE 7

Ficus and phylodendron plants were treated, when their leaves started to wither, with a 0.2% by weight aqueous solution of S-methyl-methionine sulphonium chloride. Some days after the color of the leaves turned deep green again, the chlorotic spots disappeared, and the leaflets started to intense growth.

EXAMPLE 8

Soybean plants growing on a parcel of 5 hectares were treated, at their development stage of 6–8 leaves, with a 0.2% by weight aqueous solution of S-methyl-methionine sulphonium chloride. The active agent was applied onto the plants at a rate of 0.5 kg/hectare. The treatment was repeated one week after flowering. A crop yield of 2,750 kg/hectare, calculated as dry soybean seed, was obtained on the treated parcel, whereas the crop yield obtained on the control parcel, calculated as dry substance, was only 2,500 kg/hectare.

What we claim is:

1. A method of increasing plant yield, which comprises the step of applying to the plant during a stage of intense development, or directly after flowering, 0.001 to 10 kg/ha of a salt of the Formula (I)

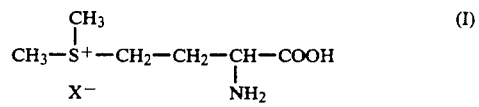

wherein $X^-$ is an agriculturally acceptable inorganic or organic ion.

2. The method of increasing plant yield defined in claim 1 wherein the agriculturally acceptable inorganic anion in the salt of the Formula (I) is derived from a mineral acid.

3. The method of increasing plant yield defined in claim 1 wherein the agriculturally acceptable organic anion in the salt of the Formula (I) is derived from a lower carboxylic acid, a long chained fatty acid, or a sulfonic acid.

4. The method of increasing plant yield defined in claim 1 wherein the salt of the Formula (I) is S-methyl-methionine sulphonium chloride.

* * * * *